US00PP14901P2

(12) United States Plant Patent
Trees

(10) Patent No.: US PP14,901 P2
(45) Date of Patent: Jun. 15, 2004

(54) VERBENA PLANT NAMED 'BALTUBURG'

(50) Latin Name: *Verbena hybrida*
Varietal Denomination: Baltuburg

(75) Inventor: Scott C. Trees, Shell Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/109,489

(22) Filed: Mar. 28, 2002

(51) Int. Cl.[7] ..... A01H 5/00
(52) U.S. Cl. ..... Plt./308
(58) Field of Search ..... Plt./308

*Primary Examiner*—Kent Bell
(74) *Attorney, Agent, or Firm*—Wood, Phillips, Katz, Clark & Mortimer

(57) ABSTRACT

A new and distinct Verbena plant named 'Baltuburg', characterized by its burgundy flowers, spreading and trailing habit, and sharply lobed, dark green leaves.

1 Drawing Sheet

Latin name of genus and species of plant claimed: *Verbena hybrida.*
Variety denomination: 'Baltuburg'.

BACKGROUND OF THE INVENTION

The present invention comprises a new and distinct verbena plant, botanically known as *Verbena hybrida*, and hereinafter referred to by the cultivar name 'Baltuburg'.

The new cultivar was developed by the inventor in a controlled breeding program during 1998, at Arroyo Grande, Calif. The objective of the breeding program was the development of verbena cultivars with a spreading and trailing habit, continuous flowering, excellent basal branching and dark green foliage.

The female or seed parent of 'Baltuburg' was the verbena variety 'SUNVP-SU' (U.S. Plant Pat. No. 10,311), which exhibits a vigorous trailing habit, scarlet flowers and medium green foliage. The male (pollen) parent of 'Baltuburg' was the proprietary verbena breeding selection PAS-984116, which exhibits a vigorous trailing habit, deep rose-red flowers and dark green foliage. 'Baltuburg' was selected in September 1999 as a single flowering plant from within the progeny of the above stated cross and was initially designated 932.

Asexual reproduction of the new cultivar, by terminal tip cuttings, was carried out during 2000 and 2001 at Arroyo Grande, Calif. and West Chicago, Ill. Such asexual propagation has demonstrated that the characteristics of the new cultivar as herein described are firmly fixed and retained through successive generations of such asexual propagation.

SUMMARY OF THE INVENTION

It was found that the cultivar of the present invention:

(a) exhibits burgundy flowers;

(b) forms sharply lobed, dark green foliage;

(c) exhibits a good basal branching character; and (d) exhibits a spreading and trailing growth habit.

The new cultivar of the present invention can be compared to 'Balazdapi' (U.S. Plant Pat. No. 12,807). In side-by-side comparison, the new cultivar has fewer flowers per inflorescence and the flowers are more red than the flowers of 'Balazdapi'.

BRIEF DESCRIPTION OF PHOTOGRAPHS

The accompanying photographs show as nearly true as it is reasonably possible to make the same in color illustrations of this type, typical flower and foliage characteristics of the new cultivar. The plants were grown for approximately 10 weeks in a greenhouse at West Chicago, Ill.

DETAILED BOTANICAL DESCRIPTION

Figure 1:
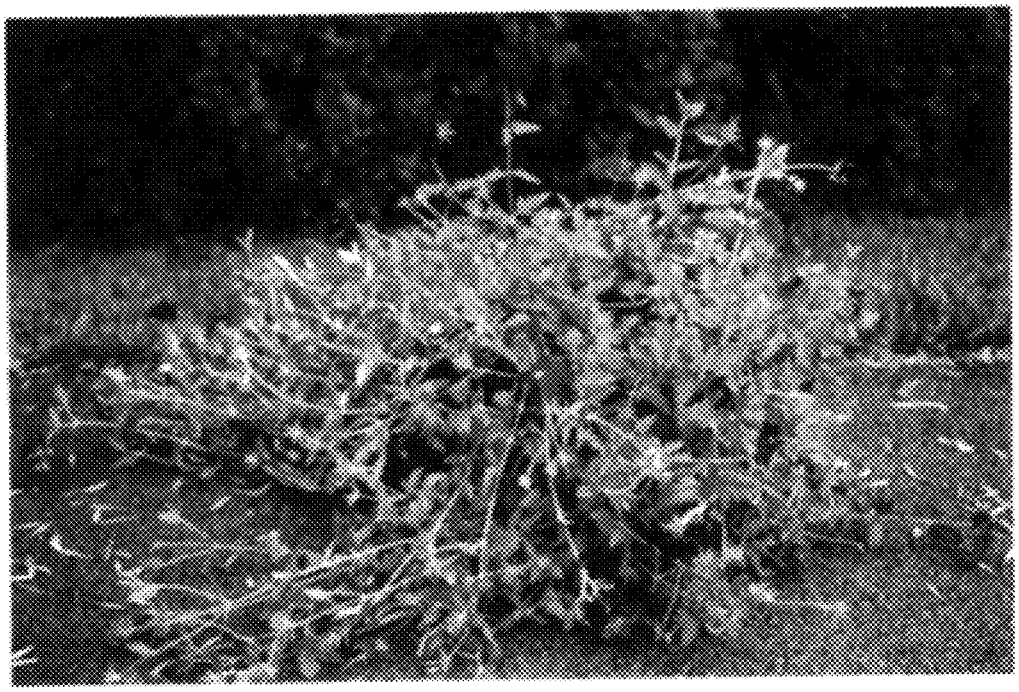
FIG. 1 shows a mature plant, exhibiting its characteristic spreading growth habit.
Figure 2:
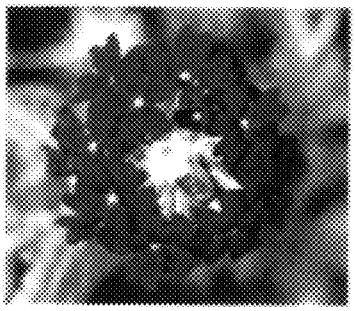
FIG. 2 shows a close-up of an individual inflorescence in full bloom.
Figure 3:
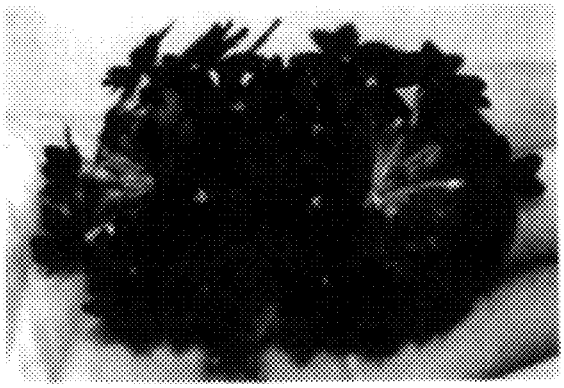
FIG. 3 shows a close up of inflorescences.

'Baltuburg' has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Feb. 15, 2002. The readings were taken between 1:00 and 3:00 p.m. under natural daylight conditions. The plants were produced from cuttings taken from stock plants and were grown in a double polycarbonate covered greenhouse under conditions comparable to those used in commercial practice. The plants were grown for 14 weeks while utilizing a soilless growth medium and maintaining temperatures of approximately 70° to 80° F. (21° to 26° C.) during the day and approximately 62° to 65° F. (17° to 18° C.) during the night and light levels above 5,000 footcandles. The following observations and measurements describe plants grown at West Chicago, Ill.

Classification:
*Botanical.*—*Verbena hybrida* cultivar 'Baltuburg'.
Parentage:
*Female parent.*—'SUNVP-SU'.
*Male parent.*—Proprietary breeding selection PAS-984116.

Propagation:

*Type cutting.*—Terminal tip.

*Time to initiate roots.*—Approximately 14–21.

*Root description.*—Fibrous, branching.

Plant description:

*Habit of growth.*—Moderately vigorous with good basal branching. Pinching improves basal branching. A mature plant, 14 weeks after the planting of a rooted cutting, measures approximately 10.1 cm in height and approximately 39.3 cm in width.

*Form.*—Mounded, trailing and spreading.

*Stem.*—Tetragonal, approximately 67 cm in length and 2 mm in diameter, with dense pubescence. Color is 146D. Internode length at middle of stem is approximately 3.5 cm. Roots tend to form at internodes.

*Foliage.*—Leaves are opposite, ovate with sharply lobed margin, acute apex and attenuate base. Upper and lower surfaces are densely covered with short, stiff hairs. Veins of lower surface are very densely pubescent. Leaf length is approximately 4.5 cm in length and approximately 3.2 cm at widest point. Upper surface is 139B and lower surface is 137C. Upper and lower surfaces have pinnate-reticulate venation. Color of venation on upper surface is 144C. Color of venation on lower surface is 139D. Petiole surface is densely pubescent, length is approximately 9 mm, diameter is 3 mm and color is 139D.

Flowering description:

*Flowering habit.*—Freely flowering.

*Natural flowering season.*—Year round in greenhouse environment and spring through autumn in outdoor garden.

*Inflorescence type.*—Type: Corymb. Size: Approximately 3.4 cm deep and approximately 5 cm in diameter with an average of 19.6 fully open flowers per inflorescence at any one time. Lastingness of individual bloom: Approximately 10 to 14 days.

*Peduncle.*—Length is approximately 7.4 cm, diameter is approximately 2 mm, surface is densely pubescent and color is 146D.

*Bud.*—Round, approximately 3 mm in diameter and 72A in color.

*Petals.*—Five, non overlapping, flat and fused at base forming a corolla tube. Shape: Obovate. Apex: Emarginate. Margin: Entire.

*Corolla.*—Diameter is approximately 2.2 cm. Petal length is 1 cm and width is 8 mm. Color of upper surface of petals when first open is redder than 79A. When fully open the upper surface is darker than 71A. Lower surface of petals is 72A at margin, 72B for next ⅔ of length and 155D at base around tube opening. Whiskers of 77C surround the opening of the corolla tube. Petal color fades to 79A with age.

*Corolla tube.*—Length is approximately 2.1 cm, diameter at tube opening is 2 mm and diameter at base is 1.5 mm. Outer surface is slightly pubescence but becomes dense near opening. Pubescence of inner surface is moderate. Color of inner and outer surfaces is 145D.

*Sepals.*—Five, fused to form calyx. Sepal apex: Acute. Sepal margin: Entire. Calyx lenth is approximately 9 mm in length, diameter at base is 2 mm and diameter at apex is 3 mm. Outer surface of sepals is densely pubescent and 144A. Inner of sepals is smooth and 144C.

*Reproductive organs.*—There are 4 stamens fused to the corolla tube. Two are positioned even with the stigma and two are positioned below the stigma. The anther length is approximately 2 mm and the color is 144B. Pollen is abundant and 2B in color. There is one pistil, 2 cm in length. The stigma length is approximately 3 mm and the color is 144A. The style length is approximately 1.5 cm and the color is 144D. Ovary length is approximately 2 mm and 144A.

Seed production: Seed production has not been observed.

Disease resistance: Reistance to pathogens common to verbena has not been observed.

I claim:

1. A new and distinct cultivar of *Verbena hybrida* plant named 'Baltuburg' substantially as herein shown and described, which:

(a) exhibits burgundy flowers;

(b) sharply lobed, dark green foliage;

(c) exhibits a good basal branching character; and (d) exhibits a spreading and trailing growth habit.

* * * * *